March 11, 1952 H. P. CONNELL Plant Pat. 1,078
CAMELLIA PLANT
Filed Dec. 6, 1950
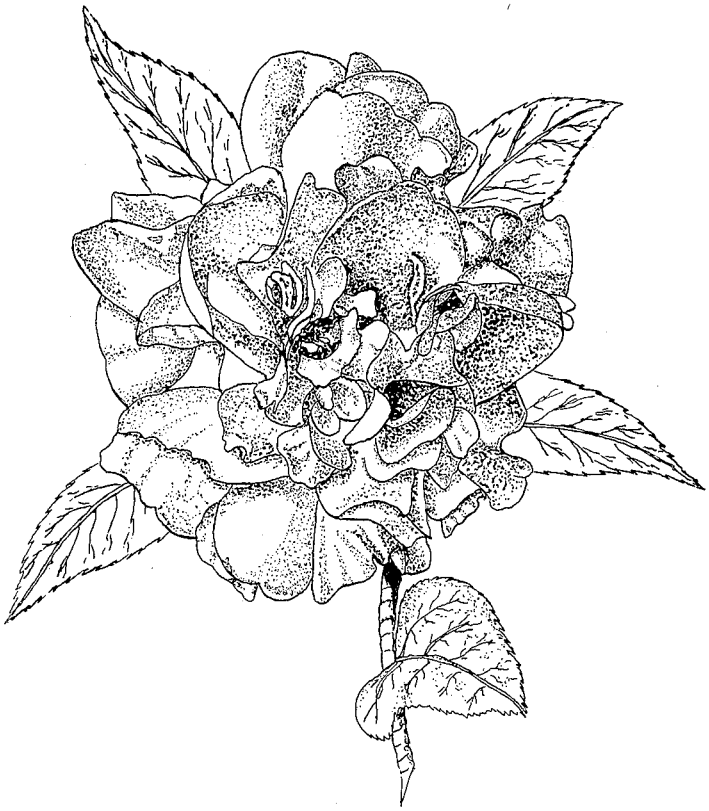
INVENTOR
Hooper P. Connell
BY Cushman, Darby & Cushman
ATTORNEY Patented Mar. 11, 1952

Plant Pat. 1,078

UNITED STATES PATENT OFFICE 1,078

CAMELLIA PLANT

Hooper P. Connell, Baton Rouge, La.

Application December 6, 1950, Serial No. 199,473

1 Claim. (Cl. 47—60)

The present invention relates to a new and distinct variety of camellia plant, having a pure white flower of dominant characteristics as described herein, including the informal arrangement of the petals in slightly waved and twisted formation, and the absence of visible stamens or petaloids at any stage of development of the flower.

The plant of the present invention was initially asexually reproduced by grafting scions from a sporting branch which exhibited the distinctive characteristics referred to herein, said sporting branch having appeared on a camellia japonica, of the variety Alba Plena not a patented variety, in my garden at Baton Rouge, Louisiana.

The present invention, therefore, is a new and distinct variety of camellia japonica. It is similar to the variety of which it was a mutation, i. e., Alba Plena, except for the distinctive characteristics referred to herein.

This new and distinct variety was first discovered by me in my garden at Baton Rouge, Louisiana, where I have had under cultivation and experimentation many varieties of camellia. Among these was a forty-year-old Alba Plena plant which I cultivated and experimented with in order to improve the variety by selection of superior characteristics for reproduction. The new variety of camellia described herein appeared as a mutation on one part of the forty-year-old Alba Plena plant which was then under cultivation and improvement in my garden at Baton Rouge, Louisiana.

Upon noting the distinctive characteristics of the camellias on the sporting branch of the Alba Plena plant, as referred to, I kept it under close observation and some months thereafter, I grafted several scions from the sporting branch on to twelve-year-old Rubra Virginalis stock in my garden, and thereafter flowers were produced by these grafted plants which were substantially identical with the flowers on the sporting branch of the original Alba Plena. By continued close observation of the plants thus grafted, I have determined that the new variety of camellia, asexually reproduced as referred to, will and does retain the distinct features described herein. Continued observation of the growth of the new plants, asexually reproduced as referred to above, indicates that they possess a stronger, more thrifty, and vigorous habit of growth, as compared with the Alba Plena variety from which they were derived. The sporting branch on the old Alba Plena plant has continued to produce the same distinct flower, and I have determined that the new flower, as it appears on the sporting branch of the old Alba Plena, and on the asexually reproduced plants, is fixed and permanent in its new characteristics, differing from the Alba Plena variety and from all other white camellia by reason of the characteristics set forth herein.

The new variety combines a number of features not heretofore found together in any camellia plant, which features result in a flower having a most distinctive and impressive appearance, and which is readily distinguishable from all other varieties of camellia. In the drawing, which discloses the new variety, the single figure is a view of the flower of the new variety of plant, looking inwardly toward the front face thereof. The distinctive features include the following:

1. *Form and size of flowers.*—The flowers are hemispherical, of full, informal peony type. They are of 4½″ diameter and 2½″ depth, maximum, and 3⅓″ in diameter and 2″ in depth, at a minimum. All petals are large, broad, about 2½″ long, not recurving, slightly wavy, firm texture, and snowy white.

2. Approximately 75 petals, long and wide, slightly waved and twisted, arranged near center in a distinct swirled formation.

3. No stamens or petaloids are visible in the flower at any stage of its development to peak growth. Only when dissected or when the parts of the flower are manually spread apart after it has reached or passed its peak of growth can several stamens ¼″ long be found deeply imbedded in the base of the flower, and at this time, several petaloids may also be found.

4. The new variety differs from the conventional Alba Plena, and from such camellias as disclosed in Plant Patent 431, Sawada, of November 19, 1940, in that these previously known varieties of camellia are of the formal type, or imbricated, producing a flat form of flower.

5. The flower of the new variety is hemispherical, with large, long, wide, wavy petals, 75 in number, making a full, deep, luxuriant flower.

6. The flower of the new variety has the appearance of a very full white peony, except for the marked swirled arrangement of the petals at the center, a feature not present in any other white camellia, insofar as I am aware.

7. The flower of the new variety never does display stamens. Some 5 or 6 stamens ¼″ long can be found deeply imbedded in the base of the flower when dissected.

The flower of the new variety is extremely full in its petalage, and is snow white. The plant blooms in the later part of December, and through January into February. The plant is an upright grower. The buds are globular. The new variety of plant has proved to be a stronger, more vigorous grower than the Alba Plena. It is not difficult to graft successfully. The numerous large petals, slightly wavy in form and arrangement, hold together as a whole firmly. The blossoms do not bruise easily due to their firm substance. No traces of color are found in the flowers, same being snow white throughout. The petals of the flowers are not arranged in definite rows. The petals do not diminish in size toward the base.

Having described my invention or discovery as completely as it is reasonably possible for me to do, I claim:

A new and distinct variety of camellia plant, having a snow white flower with informally arranged petals, the petals being slightly waved and twisted and having a distinct swirling formation near the center of the flower, the flower being further characterized by the absence of visible stamens during the growth of the flower.

HOOPER P. CONNELL.

REFERENCES CITED

The following references are of record in the file of this patent:

UNITED STATES PATENTS

| Number | Name | Date |
|---|---|---|
| Pl. Pt. 866 | Hagler | Aug. 23, 1949 |